United States Patent [19]

Parg et al.

[11] 4,239,697

[45] Dec. 16, 1980

[54] O-SUBSTITUTED N-HYDROXYSULFAMID ACID HALIDES AND THEIR PREPARATION

[75] Inventors: Adolf Parg, Bad Durkheim; Gerhard Hamprecht, Weinheim, both of Fed. Rep. of Germany

[73] Assignee: BASF Aktiengesellschaft, Fed. Rep. of Germany

[21] Appl. No.: 80,506

[22] Filed: Oct. 1, 1979

Related U.S. Application Data

[62] Division of Ser. No. 38,172, May 11, 1979.

[51] Int. Cl.$^3$ .................. C07C 143/14; C07C 143/21
[52] U.S. Cl. ............................. 260/543 R; 562/430; 544/11
[58] Field of Search ................................ 260/543 R

[56] References Cited

U.S. PATENT DOCUMENTS

| 3,555,055 | 1/1971 | Kaplan | 260/543 R |
| 3,869,509 | 3/1975 | Kuhl et al. | 260/543 R |
| 4,043,863 | 8/1977 | Bjorklund et al. | 260/543 R |

OTHER PUBLICATIONS

Traube et al, Berichte, vol. 53, pp. 1477–1492 (1920).

*Primary Examiner*—James H. Reamer
*Attorney, Agent, or Firm*—Keil & Witherspoon

[57] ABSTRACT

Novel O-substituted N-hydroxysulfamic acid halides and a process for their preparation by reacting sulfamic acids with acid halides in certain molar ratios. The compounds obtainable by the process of the invention are valuable materials for the preparation of crop protection agents, dyes and drugs.

6 Claims, No Drawings

O-SUBSTITUTED N-HYDROXYSULFAMID ACID HALIDES AND THEIR PREPARATION

This is a division, of application Ser. No. 38,172, filed May 11, 1979.

The present invention relates to novel O-substituted N-hydroxysulfamic acid halides and to a process for their preparation by reacting sulfamic acids with acid halides in certain molar ratios.

German Laid-Open Application DOS No. 2,164,176 discloses that N-alkyl- and N-cycloalkyl-sulfamic acid halides can be prepared by reacting sulfamic acids with an acid halide of sulfurous acid, phosphoric acid, phosphorous acid, carbonic acid or oxalic acid. Thionyl chloride, thionyl bromide, phosphorous pentochloride, phosphorus trichloride, phosphorus oxychloride, phosphorus pentabromide, phosphorus tribromide, phosgene, oxalic acid chloride and oxalic acid bromide are disclosed as preferred acid halides. As shown by the examples, only one acid halide at a time is used. Other than phosgene and phosphorus pentachloride, which each occur in one Example, only thionyl chloride is illustrated as a halide starting material in the remaining Examples. The DOS expressly teaches that the reaction requires the use of at least the stoichiometric amount of acid halide, but preferably a ratio of from 1.1 to 2 moles of acid halide per mole of starting material II, and that the reaction is only carried out with sulfamic acid halides which are monosubstituted at the nitrogen, the substituents being aliphatic and cycloaliphatic radicals attached by a carbon atom.

Houben-Weyl, Methoden der Organischen Chemie, Volume VI/3, page 123, discloses that the reaction of ethers with sulfuryl chloride preferentially results in chlorination at the α-carbon atom; elimination of HCl, involving the β-hydrogen, results in more highly chlorinated products also being produced via the vinyl ethers; for example, diethyl ether gives ethyl 1,2-dichloroethyl ether. O-Substituted organic hydroxylamines with thionyl chloride give sulfoxido compounds (loc. cit., Volume X/1, page 1,263):

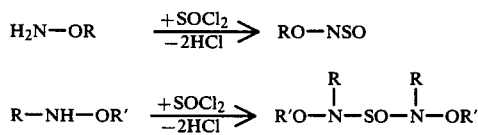

O-Hydroxylamines react with phosgene (loc. cit., Volume X/1, page 1,262) at 20° C. to give N-chlorocarbonyl-O-hydroxylamines, whilst at elevated temperatures (120°-125° C.) the reaction principally yields 1,3,5-hydroxy-2,4,6-trioxo-hexahydro-1,3,5-triazines which are etherified in the 1,3,5-position.

We have found that a O-substituted N-hydroxysulfamic acid halide of the formula

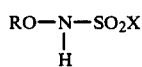

where R is an aliphatic or cycloaliphatic radical and X is halogen is obtained in an advantageous manner by reaction of a sulfamic acid with an acid halide if a sulfamic acid of the formula

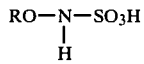

where R has the above meaning, or a metal salt thereof, is reacted with an acid halide of sulfurous acid, phosphoric acid, phosphorous acid, carbonic acid or oxalic acid, using from 0.5 to 1 mole of acid halide per mole of starting material II.

We have also found the novel O-substituted N-hydroxysulfamic acid halides of the formula

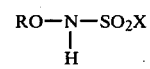

where R is an aliphatic or cycloaliphatic radical and X is halogen. Amongst these, preferred compounds are the novel sulfamic acid chlorides of the formula

where R is alkyl of 1 to 7 carbon atoms, especially O-methyl-N-hydroxysulfamic acid chloride, O-ethyl-N-hydroxysulfamic acid chloride and O-n-heptyl-N-hydroxysulfamic acid chloride.

Where the sodium salt of O-ethyl-N-hydroxysulfamic acid is used, the reaction can be represented by the following equation:

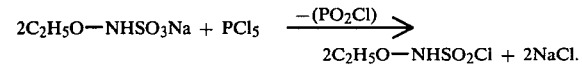

The process according to the invention gives the novel O-substituted N-hydroxysulfamic acid halides in a simple and economical manner and in good yield and high purity. The reaction time is short and the working up of the reaction mixture is simple and reliable, particularly with a view to protection of the environment. All these advantageous results are surprising in the light of the prior art.

The starting materials II can for example be prepared in the form of the alkali metal salt of the O-alkyl-N-hydroxysulfamic acid by a process of W. Traube, H. Ohlendorf and H. Zander (Berichte der deutschen Chemischen Gesellschaft, 53 (1920), 1,477–1,492). They can also be prepared by a process similar to that described for N-alkylsulfamates in J. Am. Chem. Soc., 73 (1951), 5,507, by reacting a O-substituted hydroxylamine with sulfur trioxide or amidosulfonic acid.

Preferred starting materials II and accordingly preferred end products I are those where R is straight-chain or branched alkyl of 1 to 20, especially 1 to 8, carbon atoms, or is alkyl of 2 to 20, especially 2 to 8, advantageously 2 to 6, carbon atoms which is substituted by several alkoxy groups, preferably 3 or 2 alkoxy groups, and especially 1 alkoxy group of 1 to 7, especially 1 to 3, carbon atoms, or is cycloalkyl of 4 to 8 carbon atoms, and X is fluorine or especially chlorine. The said radicals may in addition be substituted by groups and/or atoms which are inert under the reaction conditions, for example chlorine, bromine, alkyl or alkoxy each of 1 to 4 carbon atoms, carbalkoxy of 2 to 4 carbon atoms or cycloalkyl of 4 to 6 carbon atoms. Preferred starting materials II and end products I are especially those where R is methyl, ethyl, n-propyl, iso-propyl, n-butyl, iso-butyl, sec.-butyl, n-pentyl, n-hexyl or n-heptyl.

Examples of suitable sulfamic acids II are O-methyl-N-hydroxysulfamic acid, O-ethyl-N-hydroxysulfamic acid, O-n-propyl-N-hydroxysulfamic acid, O-isopropyl-N-hydroxysulfamic acid, O-n-butyl-N-hydroxysulfamic acid, O-isobutyl-N-hydroxysulfamic acid, O-sec.-butyl-N-hydroxysulfamic acid, O-(1-ethyl)-n-propyl-N-hydroxysulfamic acid, O-(1,2-dimethyl)-n-propyl-N-hydroxysulfamic acid, O-n-pentyl-N-hydroxysulfamic acid, O-cyclopentyl-N-hydroxysulfamic acid, O-n-hexyl-N-hydroxysulfamic acid, O-hex-3-yl-N-hydroxysulfamic acid, O-cyclohexyl-N-hydroxysulfamic acid, O-hept-4-yl-N-hydroxysulfaic acid, O-(2-methyl-1-ethyl)-n-propyl-N-hydroxysulfamic acid, O-(1,2,2-trimethyl)-n-propyl-N-hydroxysulfamic acid, O-(1,3-dimethyl)-n-butyl-N-hydroxysulfamic acid, O-(1,2-dimethyl)-n-butyl-N-hydroxysulfamic acid, O-(1,2-dimethyl)-n-hexyl-N-hydroxysulfamic acid, O-(1-cyclohexyl)ethyl-N-hydroxysulfamic acid, O-2-chloroisopropyl-N-hydroxysulfamic acid, O-2-chloropropyl-N-hydroxysulfamic acid, O-3-chloropropyl-N-hydroxysulfamic acid, O-3-bromopropyl-N-hydroxysulfamic acid and O-(1-chloromethyl)-n-propyl-N-hydroxysulfamic acid; O-tert.-butyl-, O-pent-2-yl-, O-n-heptyl-, O-n-octyl-, O-n-nonyl-, O-n-decyl-, O-2-ethylhexyl-, O-2-ethylpentyl-, O-3-ethylpentyl-, O-2,3-dimethyl-n-butyl-, O-2-methylpentyl-, O-3-methylpentyl-, O-2-methylheptyl-, O-3-methylheptyl-, O-4-methylheptyl-, O-3-ethylhexyl-, O-2,3-dimethylhexyl-, O-2,4-dimethylhexyl-, O-2,5-dimethylhexyl-, O-undecyl-, O-dodecyl-, O-tridecyl-, O-tetradecyl-, O-pentadecyl-, O-hexadecyl-, O-heptadecyl-, O-octadecyl-, O-nona-decyl- and O-eicosyl-N-hydroxysulfamic acid; the ω-methoxy-, ω-ethoxy-, ω-n-propoxy-, ω-isopropoxy-, ω-n-butoxy-, ω-isobutoxy-, ω-sec.-butoxy-, ω-tert.-butoxy-, ω-pentoxy-, ω-pent-2-oxy-, ω-pent-3-oxy-, ω-n-hexoxy and ω-n-heptoxy compound of O-ethyl-, O-n-propyl-, O-isopropyl-, O-n-butyl-, O-isobutyl-, O-sec.-butyl-, O-tert.-butyl-, O-pentyl-, O-pent-2-yl-, O-pent-3-yl-, O-n-hexyl-, O-n-heptyl-, O-n-octyl-, O-n-nonyl-, O-n-decyl-, O-2-ethylhexyl-, O-2-ethylpentyl-, O-3-ethylpentyl-, O-2,3-dimethyl-n-butyl-, O-2-methylpentyl-, O-3-methylpentyl-, O-2-methylheptyl-, O-3-methylheptyl-, O-4-methylheptyl-, O-3-ethylhexyl-, O-2,3-dimethylhexyl-, O-2,4-dimethylhexyl-, O-2,5-dimethylhexyl-, O-undecyl-, O-dodecyl-, O-tridecyl-, O-tetradecyl-, O-pentadecyl-, O-hexadecyl-, O-heptadecyl-, O-octadecyl-, O-nonadecyl- and O-eicosyl-N-hydroxysulfamic acid and corresponding methyl-, ethyl-, n-propyl-, isopropyl-, n-butyl-, isobutyl-, sec.-butyl-, tert.-butyl-, pentyl-, pent-2-yl-, pent-3-yl-, n-hexyl- and n-heptyl-ethers in the 1- or 2-position of O-n-propyl-, O-isopropyl-, O-n-butyl-, O-isobutyl-, O-sec.-butyl, O-tert.-butyl-, O-pentyl-, O-pent-2-yl-, O-pent-3-yl-, O-n-hexyl-, O-n-heptyl-, O-n-octyl-, O-n-nonyl-, O-n-decyl-, O-2-ethylhexyl-, O-2-ethylpentyl-, O-3-ethylpentyl-, O-2,3-dimethyl-n-butyl-, O-2-methylpentyl-, O-3-methylpentyl, O-2-methylheptyl-, O-3-methylheptyl-, O-4-methylheptyl-, O-3-ethylhexyl-, O-2,3-dimethylhexyl-, O-2,4-dimethylhexyl-, O-2,5-dimethylhexyl-, O-undecyl-, O-dodecyl-, O-tridecyl-, O-tetradecyl-, O-pentadecyl-, O-hexadecyl-, O-octadecyl-, O-nonadecyl- and O-eicosyl-N-hydroxysulfamic acid or in the 1-position of O-ethyl-N-hydroxysulfamic acid.

The starting materials II can be used in the form of sulfamic acids or of metal sulfamates. Preferred metal salts are the alkali metal salts or alkaline earth metal salts, eg. the magnesium, calcium, lithium, potassium and especially sodium sulfamate.

The starting materials II are reacted with the acid halide in a ratio of from 0.5 to 1, preferably from 0.8 to 1, mole of acid halide per mole of starting material II. Preferred acid halides are those of the general formula $$Z-X \qquad \qquad III$$

where X is chlorine or fluorine and Z is the acyl radical of one of the above acids, advantageously thionyl chloride, thionyl fluoride, sulfur tetrafluoride, phosgene, oxalic acid chloride and especially phosphorous pentachloride, phosphorus trichloride and phosphorus oxychloride.

The acid halide used, or a mixture of acid halides, especially a mixture in which a phosphorus oxyhalide is one component, can serve as the solvent in the process according to the invention. However, the reaction is advantageously carried out in an organic solvent which is inert under the reaction conditions. Suitable solvents which are inert under the reaction conditions are halohydrocarbons, especially chlorohydrocarbons, eg. tetrachloroethylene, 1,1,2,2- and 1,1,1,2-tetrachloroethane, amyl chloride, cyclohexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1- and 1,1,2-trichloroethane, trichloroethylene, pentachloroethane, 1,2-cis-dichloroethylene, 1,2-dichloroethane, 1,1-dichloroethane, n-propyl chloride, n-butyl chloride, 2-, 3- and isobutyl chloride, chlorobenzene, fluorobenzene, bromobenzene, iodobenzene, o-, p- and m-dichlorobenzene, o-, p- and m-dibromobenzene, o-,m- and p-chlorotoluene, 1,2,4-trichlorobenzene, 1,10-dibromodecane and 1,4-dibromobutane; aliphatic or cycloaliphatic ethers, eg. n-butyl ethyl ether, di-n-butyl ether, di-iso-amyl ether, diisopropyl ether, cyclohexyl methyl ether, diethyl ether, tetrahydrofuran, dioxane and β,β'-dichlorodiethyl ether; nitriles, eg. acetonitrile, propionitrile, butyronitrile, isobutyronitrile, benzonitrile and o-, m- and p-chlorobenzonitrile; aliphatic and cycloaliphatic hydrocarbons, eg. pentane, hexane, heptane, nonane, α-pinene, o-, m- and p-cimene, gasoline fractions, especially of boiling point from 70° to 190° C., cyclohexane, methylcyclohexane, petroleum ether, decalin, naphtha, 2,2,4-trimethylpentane, 2,2,3-trimethylpentane, 2,3,3-trimethylpentane and octane; aromatic hydrocarbons, eg. benzene, toluene, ethylbenzene, o-, m- and p-xylene and mesitylene; and mixtures of these. Advantageously, the solvent is used in an amount of from 20 to 1,000, preferably from 35 to 300, especially from 65 to 150, percent by weight, based on starting material II.

The reaction is as a rule carried out at from −10° to +130° C., preferably from 10° to 120° C., especially from 50° to 100° C., under atmospheric or superatmospheric pressure, continuously or batchwise.

The reaction may be carried out as follows: a mixture of starting material II, acid halide and solvent is kept at the reaction temperature for from 2 to 8 hours. It is possible to mix the acid chloride or the starting material II with the solvent and then to add the other component. The end product I is isolated from the reaction mixture by conventional methods, for example by fractional distillation. In an advantageous embodiment, a mixture is prepared of, for example, a suspension of the sulfamic acid II or of a salt thereof and one of the above halohydrocarbons, advantageously using from 65 to 300 percent by weight of the latter, based on starting material II; to this mixture, prepared, for example, at 15°–35° C., is then added the acid halide, preferably phosphorus pentachloride, from a metering device. However, it is also possible, for example, to suspend phosphorus pentachloride in phosphorus oxychloride and then run this mixture into a suspension of the sulfamic acid II in one of the above inert halohydrocarbons. Instead of phosphorus pentachloride, one of its starting materials can also advantageously be used. For example, the calculated amount of chlorine may be passed into a solution of phosphorus trichloride in phosphorus oxychloride, using the process described in U.S. Pat. No. 1,906,440, after which the resulting suspension is run into a suspension of the sulfamic acid II in one of the above inert halohydrocarbons. However, using the method of the above patent, it is also possible to treat a mixture of yellow phosphorus in phosphorus oxychloride with the calculated amount of chlorine and then to introduce the product into the sulfamic acid suspension.

The following procedure is preferred: the acid halide is added, with vigorous stirring, to a mixture of starting material II and solvent, advantageously in the course of from 10 to 55 minutes, and commonly at from 20° to 50° C.; the reaction thereafter takes place at not less than 50° C.

The compounds obtainable by the process of the invention are valuable starting materials for the preparation of crop protection agents, dyes and drugs. For example, O-substituted N-hydroxy-o-sulfamidobenzoic acids can be prepared from them by reaction with anthranilic acid or its salts, in accordance with the process of German Laid-Open Application DOS No. 2,104,682. Cyclization of these compounds, for example by the process described in German Laid-Open Application DOS No. 2,105,687, gives the corresponding 2,1,3-benzothiadiazin-4-one-2,2-dioxides, which may be used in order to prepare crop protection agents and drugs.

Other herbicides are obtained by reacting the end products I with substituted glycolic acid anilides.

The end products I stated above to be preferred are also preferred compounds for the above uses.

In the Examples which follow, parts are by weight.

EXAMPLE 1

208 parts of phosphorus pentachloride are introduced into a stirred suspension of 149 parts of sodium O-methyl-N-hydroxysulfamate in 1,000 parts of 1,2-dichloroethane at 22° C. The reaction mixture is then heated to 75° C. in the course of 30 minutes, and is stirred at 75°–80° C. for 2 hours. Thereafter it is filtered and the filtrate is freed from 1,2-dichloroethane under reduced pressure; fractional distillation of the residue gives 101 parts (70% of theory) of O-methyl-N-hydroxysulfamic acid chloride of boiling point 46°–48° C./0.2 mbar and $n_D^{25}$: 1.4527.

EXAMPLE 2

52 parts of phosphorus pentachloride are introduced from a metering device into a stirred suspension of 41 parts of sodium O-ethyl-N-hydroxysulfamate in 45 parts of phosphorus oxychloride and 70 parts of benzene at 0° C. The reaction mixture is then heated to 80° C. in the course of 30 minutes and stirred at 80°–82° C. for 2 hours. Fractional distillation of the reaction mixture gives 23.8 parts (60% of theory) of O-ethyl-N-hydroxysulfamic acid chloride of boiling point 58°–62° C./0.2 mbar and $n_D^{25}$: 1.4495.

EXAMPLE 3

208 parts of phosphorus pentachloride suspended in 500 parts of 1,2-dichloroethane are introduced from a metering device into a suspension of 233 parts of sodium O-n-heptyl-N-hydroxysulfamate in 500 parts of 1,2-dichloroethane at 25° C. The reaction mixture is heated to 75° C., stirred at 75°–80° C. for 3 hours, cooled and filtered. Fractional distillation under reduced pressure gives 121 parts (53% of theory) of O-n-heptyl-N-hydroxysulfamic acid chloride of boiling point 140°–145° C./0.5 mbar and $n_D^{25}$: 1.4523.

EXAMPLE 4

52 parts of phosphorus pentachloride are introduced from a metering device into a stirred suspension of 44 parts of sodium O-isopropyl-N-hydroxysulfamate in 300 parts of chlorobenzene at 25° C. The reaction mixture is heated to 75° C., stirred for 2 hours at 75°–80° C., cooled and filtered. Fractional distillation under reduced pressure gives 25 parts (58% of theory) of O-isopropyl-N-hydroxysulfamic acid chloride of boiling point 138°–140° C./0.5 mbar and $n_D^{25}$: 1.4516.

We claim:

1. A O-substituted N-hydroxysulfamic acid halide of the formula $$RO-\underset{H}{N}-SO_2X \qquad I$$

where R is alkyl of 1 to 20 carbons, alkyl of 2 to 20 carbons substituted by 1 to 3 alkoxy groups of 1 to 7 carbons, cycloalkyl of 4 to 8 carbon atoms or said groups further substituted by chlorine, bromine, alkyl or alkoxy each of 1 to 4 carbon atoms, carbalkoxy of 2 to 4 carbon atoms or cycloalkyl of 4 to 6 carbon atoms and X is halogen.

2. A sulfamic acid chloride of the formula $$RONHSO_2Cl \qquad I$$

where R is alkyl of 1 to 7 carbon atoms.

3. O-Methyl-N-hydroxysulfamic acid chloride.
4. O-Ethyl-N-hydroxysulfamic acid chloride.
5. O-n-Heptyl-N-hydroxysulfamic acid chloride.
6. A sulfamic acid halide as set forth in claim 1 wherein X is chlorine.

* * * * *